United States Patent [19]

Herrera V. et al.

[11] Plant 4,472

[45] Oct. 30, 1979

[54] CHRYSANTHEMUM PLANT

[75] Inventors: Camilo Herrera V.; Reinaldo Saavedra, both of Bogata, Colombia

[73] Assignee: Jardines de Lose Andes Ltda., Bogata, Colombia

[21] Appl. No.: 936,017

[22] Filed: Aug. 22, 1978

[51] Int. Cl.[2] ..... A01H 5/00

[52] U.S. Cl. ..... Plt./78

[58] Field of Search ..... Plt./78

*Primary Examiner*—Robert E. Bagwill
*Attorney, Agent, or Firm*—Donald D. Jeffery

[57] ABSTRACT

A chrysanthemum plant with flat decorative capitulum which is a sport of the cultivar Firebrand (unpatented), being distiguished from the parent cultivar by its dark yellow ray floret color.

2 Drawing Figures

The present invention comprises a new and distinct cultivar of *Chrysanthemum morifolium*, Ramat., hereinafter referred to by the cultivar name of Simona.

Simona is a spontaneous mutation of the unpatented cultivar Firebrand and was selected to expand the color range of the parental variety.

Simona was discovered and selected by Camilo Herrera V. on Nov. 15, 1972, as one plant within a flowering block of Firebrand at Jardies de Los Andes, Bogata, Columbia. The first act of asexual reproduction of Simona was accomplished on Feb. 22, 1973 when vegetative cuttings were taken from the initial selection in Bogata, Columbia by Reinaldo Saavedra working under formulations established and supervised by Camilo Herrera V.

Horticultural examination of selected units initiated May 1, 1977 has demonstrated that the combination of characteristics as herein disclosed for Simona are firmly fixed and are retained through successive generations of asexual reproduction.

Simona has not been observed under all possible environmental conditions. The phenotype may vary significantly with variations in environment such as temperature, light intensity and daylength. The following observations, measurements, and comparisons describe plants grown in Bogata, Columbia and Salinas, Calif. under environmental conditions which approximate those generally used in commercial practice.

The following traits have been repeatedly observed and are determined to be basic characteristics of Simona which in combination distinguish this chrysanthemum as a new and distinct cultivar:

(1) Decorative capitulum type.

(2) Flat capitulum form.

(3) Dark yellow ray floret color.

(4) Diameter across face of inflorescence ranging from 90 to 115 mm. at maturity.

(5) Uniform ten week photoperiodic flowering response to short days.

(6) Tall plant height (requires 1-2 long day weeks prior to short days to attain a flowered plant height of 77 to 82 cm. when grown as a single stem plant for April through November flowerings in Salinas, Calif.).

(7) Semi-upright branching pattern.

The accompanying color photographic drawing comprising sheet 1 shows typical inflorescence and foliage characteristics of Simona. Some difficulty was encountered in obtaining accuracte color representation, the photographic rendition being more gold, or less yellow than the actual flower color of Simona. The color readings within the following description are, however, correct. Sheet 2 is a black and white photographic showing the spray formation of Simona.

Of the many commercial cultivars known to the present inventors, the most similar existing cultivars in comparison to Simona is the parental cultivar Firebrand.

Reference is made to attached Chart A which compares certain characteristics of Simona with the same characteristics of Firebrand. In comparison to Firebrand, Simona has different ray floret color. Other characteristics of Simona are similar to those same characteristics of Firebrand.

In the following description, color references are made to A Limit Color Cascade, published by the Munsell Company, 1972 edition. The color values were determined between 9:15 and 9:30 A.M. on June 22, 1978 under 200 foot-candle light intensity at Salinas, Calif.

Botanical classification: *Chrysanthemum morifolium*, Ramat., cv Simona.

I. INFLORESCENCE

A. Capitulum:

*Form.*—Flat.

*Type.*—Decorative.

*Permanence.*—14 to 18 days.

*Diameter across face.*—90 to 115 mm.

B. Corolla of ray florets:

*Color (abaxial).*—27-7 (immature) to 27-4 (mature).

*Color (adaxial).*—27-2 to 27-4.

C. Reproductive organs:

*Androecium.*—Present disc florets; scant pollen.

*Gynoecium.*—Present both ray and disc florets.

II. PLANT

A. General appearance: semi-upright branching pattern; tall height.

B. Foliage:

*Color (abaxial).*—Approximately 20-14 to 20-15.

*Color (adaxial).*—Approximately 22-13.

CHART A

COMPARISON OF SIMONA AND FIREBRAND

| Cultivar | Ray Floret Color | Diameter Across Face of Capitulum | Plant Height | Branching Pattern | Flowering Response Period | Capitulum Form and Type |
|---|---|---|---|---|---|---|
| Simona | Dark Yellow | 90 to 115 mm. | Tall, 77 to 82 cm. | Semi-upright | 10 week | Flat Decorative |
| Firebrand | Red Bronze | 90 to 115 mm. | Tall, 77 to 82 cm. | Semi-upright | 10 week | Flat Decorative |

-continued

CHART A

COMPARISON OF SIMONA AND FIREBRAND

Comparisons made of plants grown in Bogata, Columbia and Salinas, California.

We claim:

1. A new and distinct cultivar of *Chrysanthemum morifolium;* Ramat., known by the cultivar name Simona and particularly characterized as to uniqueness by the combined characteristics of decorative capitulum type; flat capitulum form; dark yellow ray floret color; diameter across face of capitulum from 90 to 115 mm. at maturity; uniform ten week flowering response to photoperiodic short-day control; tall plant height; and semi-upright branching pattern.

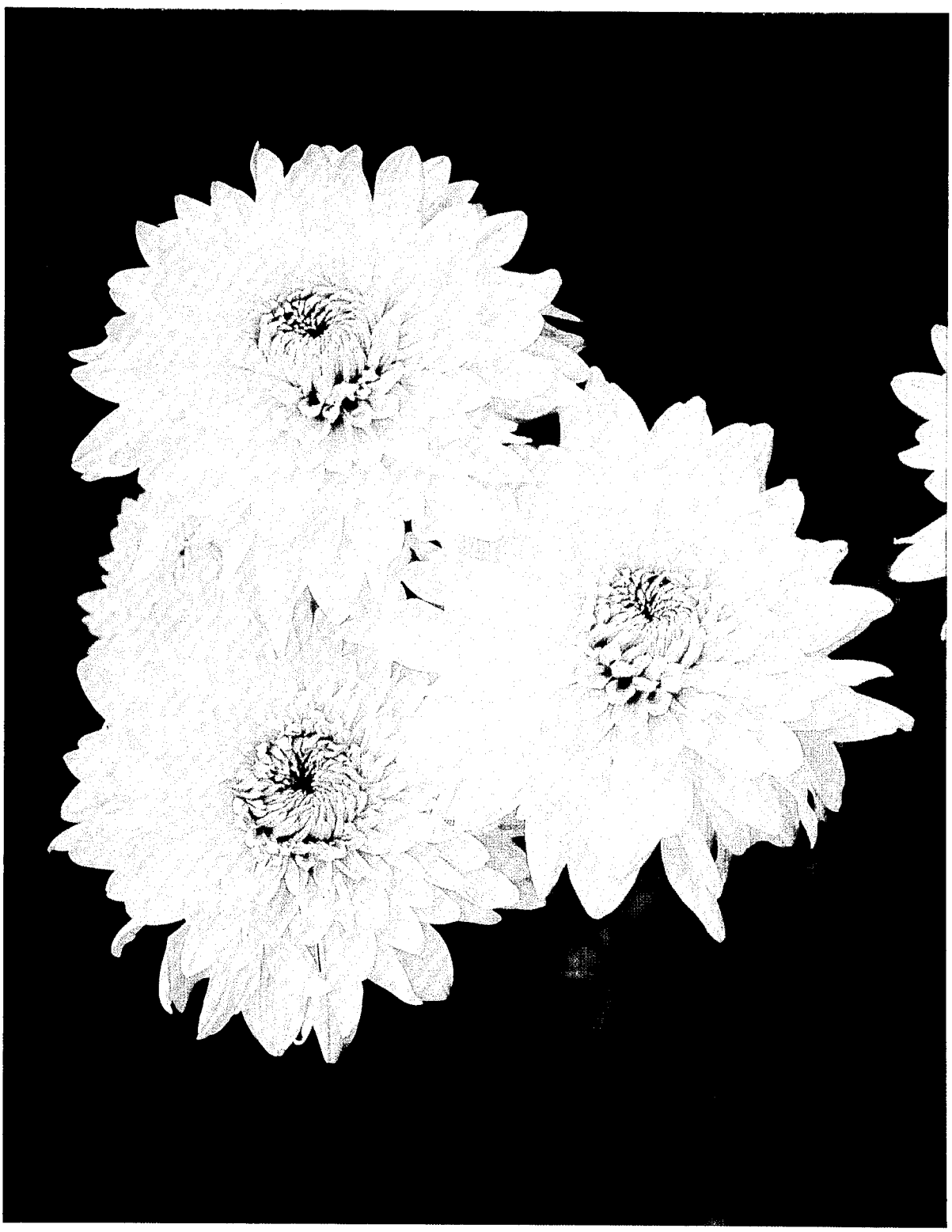

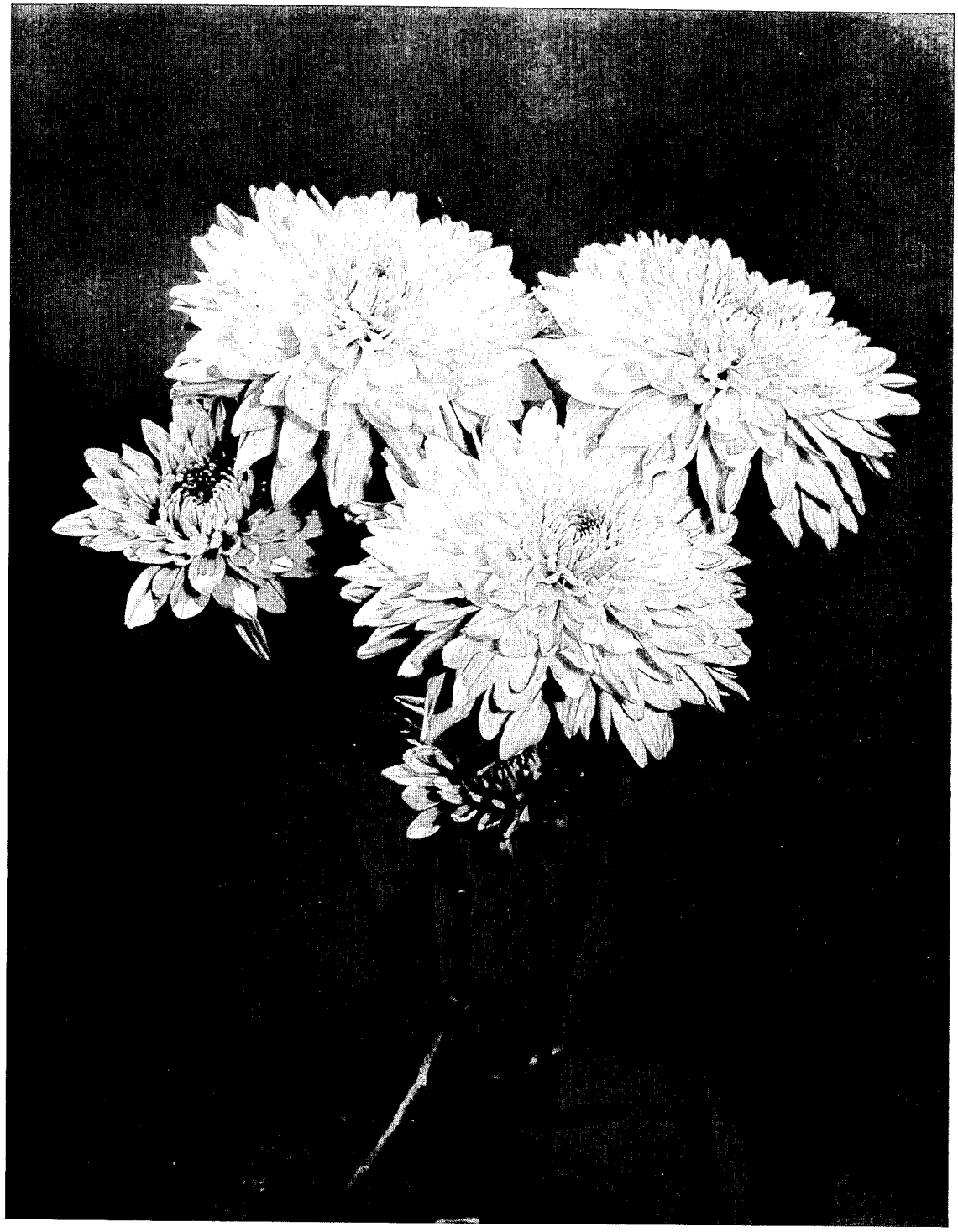

* * * * *